(12) United States Patent
Rezachek et al.

(10) Patent No.: US 8,689,607 B2
(45) Date of Patent: Apr. 8, 2014

(54) APPARATUS AND METHOD OF PHOTOACOUSTIC SENSOR SIGNAL ACQUISITION

(75) Inventors: Thomas M. Rezachek, Cottage Grove, MN (US); Gary P. Shubinsky, Buffalo Grove, IL (US); Michael Freeman, Northville, MI (US)

(73) Assignee: Honeywell International Inc., Morristown, NJ (US)

( * ) Notice: Subject to any disclaimer, the term of this patent is extended or adjusted under 35 U.S.C. 154(b) by 274 days.

(21) Appl. No.: 13/101,039

(22) Filed: May 4, 2011

(65) Prior Publication Data

US 2012/0279280 A1    Nov. 8, 2012

(51) Int. Cl.
*G01N 21/00* (2006.01)
(52) U.S. Cl.
USPC ......................................................... 73/24.02

(58) Field of Classification Search
None
See application file for complete search history.

(56) References Cited

U.S. PATENT DOCUMENTS

| | | | |
|---|---|---|---|
| 7,242,479 B2* | 7/2007 | Moeckli et al. ............... | 356/437 |
| 2005/0121614 A1 | 6/2005 | Stuttard ......................... | 250/343 |
| 2005/0160791 A1* | 7/2005 | Kung ........................... | 73/24.02 |
| 2009/0320561 A1 | 12/2009 | Fritz et al. .................... | 73/24.02 |
| 2010/0027012 A1 | 2/2010 | Fritz et al. .................... | 356/432 |
| 2010/0045998 A1 | 2/2010 | Fritz et al. .................... | 356/450 |
| 2010/0147051 A1* | 6/2010 | Tobias ......................... | 73/24.02 |
| 2010/0242572 A1* | 9/2010 | Yu ................................ | 73/24.02 |
| 2010/0253527 A1* | 10/2010 | Pellegrino et al. ............ | 340/600 |
| 2012/0039499 A1* | 2/2012 | Ryan et al. ................... | 381/369 |
| 2012/0266655 A1* | 10/2012 | Brun et al. .................. | 73/24.02 |

* cited by examiner

*Primary Examiner* — Robert R Raevis
(74) *Attorney, Agent, or Firm* — Husch Blackwell LLP

(57) ABSTRACT

A photoacoustic detector includes first and second microphones carried by an acoustic sensing chamber. Signals from the microphones are processed using lock-in detection to increase the signal-to-noise ratio. An acoustic pressure generator can be incorporated to calibrate the microphones.

12 Claims, 1 Drawing Sheet

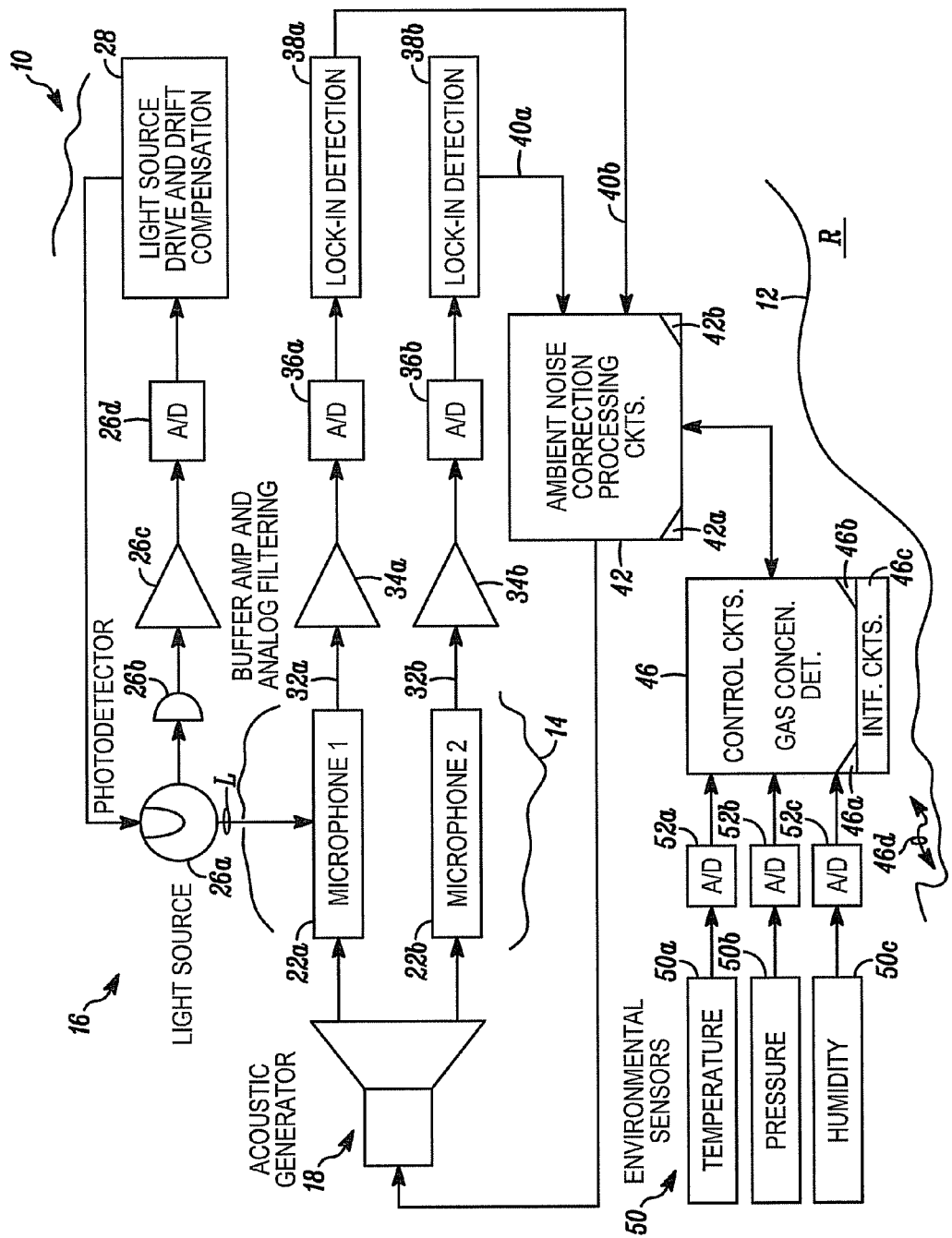

APPARATUS AND METHOD OF PHOTOACOUSTIC SENSOR SIGNAL ACQUISITION

FIELD

The application pertains to photoacoustic detectors. More particularly, the application pertains to such detectors which include multiple audio transducers and associated signal processing to provide high signal to noise ratios.

BACKGROUND

Various types of photoacoustic sensors are known to detect gases. These include, Fritz et al., US Patent Application No. 2009/0320561, published Dec. 31, 2009 and entitled "Photoacoustic Cell"; Fritz et al., US Patent Application No. 2010/0027012, published Feb. 4, 2010 and entitled, "Photoacoustic Spectroscopy System"; Fritz et al., US Patent Application No. 2010/0045998, published Feb. 25, 2010 and entitled "Photoacoustic Sensor"; and Tobias, US Patent Application No. 2010/0147051, published Jun. 17, 2010 and entitled, "Apparatus and Method for Using the Speed of Sound in Photoacoustic Gas Sensor Measurements. The above noted published applications have been assigned to the assignee hereof, and are incorporated herein by reference.

Precise signal acquisition is important for accurate gas concentration measurement using photoacoustic sensors. A high level of signal to noise ratio must be obtained from a primary light source and pressure measurement system in order to acquire a photoacoustic signal and have sufficient differentiation between the actual photoacoustic signal and background effects.

BRIEF DESCRIPTION OF THE DRAWING

FIG. 1 is a block diagram of an embodiment hereof.

DETAILED DESCRIPTION

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

A disclosed embodiment utilizes dual acoustic sensors which provide for a redundant measurement of the photoacoustic effect generated by the pulsed light source in presence of the gas. The dual microphone based signal acquisition allows measurement of singular effect via two microphones which generate different amplitudes and a phase difference with respect to each other.

A method is disclosed enabling ambient acoustic noise level to be deduced and removed from both signals. Making sure both ambient-noise corrected signals have a constant amplitude ratio and a fixed phase relationship provides an indicator that the system is operating properly.

A built-in acoustic pressure generator provides for periodic calibration of both acoustic sensors. Ambient pressure, temperature, and humidity sensors can be used to track the photoacoustic sensor's operating environment and correct its gas concentration output.

In one aspect of a disclosed implementation the signals from two microphones are individually amplified and filtered, and, then digitized. The digitized signals are then processed, for example by using lock-in detection. The lock-in reference frequency is the light source drive frequency for photoacoustic signal processing or the acoustic generator drive frequency for self-calibration processing.

The results of the lock-in detection processing can be accumulated for a predetermined period of time, typically on the order of several seconds, to provide a very high photoacoustic signal to noise ratio. The self-calibration procedure establishes a amplitude and phase relationship between the two microphones that can be used to compensate for the presence of ambient acoustic noise. The limits of this compensation can also be determined during self-calibration by attempting to null the acoustic generator signal. This enables the detector to determine when the ambient acoustic noise is too large to provide a reliable gas concentration output. By comparing the self-calibration results to those obtained during factory calibration, system degradation and failure can also be detected.

The ambient-noise-corrected photoacoustic signal can be combined with digitized temperature, pressure, and humidity environmental data to obtain a final gas concentration output signal. Concentrations of a variety of gases can be determined in accordance herewith.

FIG. 1 is a block diagram of a detector 10 in accordance herewith. The detector 10 can monitor concentrations of one or more airborne gases in an adjacent region R. Detector 10 includes a housing 12 which can carry a photoacoustic sensing chamber or cell 14.

Detector 10 includes a radiant energy emitting and control system 16 and an acoustic generator 18. Dual microphones 22 a, b are carried by or adjacent to the chamber 14 and respond to inputs from generator 18. The microphones 22a, b also respond to audio generated by radiant energy, or light L, from a source 26a. The source 26a injects light into the chamber 14 as would be understood by those of skill in the art to produce a photoacoustic audio signal, and need not be discussed further.

Feedback is provided in system 16 by a photodetector 26b which couples a signal, indicative of the output of source 26a through an amplifier and filter 26c, via an analog-to-digital converter 26d to drive and drift compensation circuits 28.

Dual channel output signals on lines 32a, b from the microphones 22 a, b can be coupled via amplifiers 34a, b to analog-to-digital converters 36a, b to lock-in detection circuits 38a, b. Output signals on lines 40a, b from the detection circuits 38a, b can be coupled to ambient noise correction processing circuits 42. Processing circuits 42 can be implemented with one or more programmable processors 42a which execute software or control programs 42b pre-stored on computer readable media such as semiconductor memory chips.

The corrected outputs can be coupled to control and processing circuits 46 which can carry out gas concentration detection. Circuits 46 can be implemented with one or more programmable processors 46a which execute software or control programs 46b pre-stored on computer readable media such as semiconductor memory chips.

Interface circuits 46c, also coupled to the control circuits 46 provide for bidirectional communication with a docking station, or a displaced monitoring system via a wired or wireless medium 46d. Environmental sensors 50a, b, c can detect ambient temperature, pressure or humidity in the vicinity of the housing 12. Signals from the sensors 50a, b, c can be digitized in analog-to-digital converters 52a, b, c and the coupled to the control circuits 46 as discussed above.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A photoacoustic detector comprising:
a sensing chamber;
first and second acoustic transducers carried adjacent to the chamber; and
circuitry coupled to the transducers,
where the circuitry receives first and second electrical signals from the two transducers,
where the circuitry includes lock-in detection circuits, which, over a predetermined time interval, process the two signals from the transducers to increase the signal-to-noise ratio thereof,
where the circuitry includes ambient noise correction processing circuits to eliminate a noise component from the processed signals and, to determine that first and second ambient-noise corrected signals, obtained from the first and second electrical signals, exhibit a constant amplitude ratio and a fixed phase relationship, and
where the circuitry includes control and processing circuits to carry out gas concentration detection.

2. A detector as in claim 1 which includes an acoustic pressure generator to direct acoustic pressure into the sensing chamber, wherein the circuitry actives the acoustic pressure generator to calibrate the transducers.

3. A detector as in claim 1 where the circuitry includes amplification and filtration circuitry and analog-to-digital converters, and where the amplification and filtration circuitry processes the first and second electrical signals and transmits the processed signals to respective ones of the analog-to-digital converters which produce first and second digitized signals.

4. A detector as in claim 3 where the lock-in detection circuits to increase the signal-to-noise ratio of the digitized signals.

5. A detector as in claim 4 which includes an acoustic pressure generator to direct acoustic pressure into the sensing chamber, wherein the circuitry activates the acoustic pressure generator to calibrate the transducers.

6. A detector as in claim 5 which includes ambient condition sensors coupled to the circuitry.

7. A detector as in claim 1 where the lock-in detection circuits increase the signal-to-noise ratio of the first and second signals.

8. A multi-channel photoacoustic detector comprising:
a multi-channel photoacoustic sensing cell which has first and second acoustic output channels;
an acoustic generator coupled to the cell;
a source of radiant energy coupled to the cell;
circuitry coupled to the output channels to enhance a signal-to-noise ratio thereof and to make a gas concentration determination based thereon; and
periodic actuation circuitry to drive the acoustic generator and produce acoustic outputs in the cell to calibrate at least one transducer in one of the output channels.

9. A detector as in claim 8 which includes a plurality of environmental sensors coupled to the circuitry.

10. A detector as in claim 8 which includes lock-in detection circuitry coupled to each of the channels.

11. A detector as in claim 10 which includes a closed loop control system to at least intermittently energize the source of radiant energy.

12. A detector as in claim 10 where each of the acoustic output channels includes an acoustic transducer.

* * * * *